(12) United States Patent
Sperling et al.

(10) Patent No.: US 12,102,541 B2
(45) Date of Patent: *Oct. 1, 2024

(54) SHOULDER PROSTHESIS WITH VARIABLE INCLINATION HUMERAL HEAD COMPONENT

(71) Applicant: Mayo Foundation for Medical Education and Research, Rochester, MN (US)

(72) Inventors: John W. Sperling, Rochester, MN (US); Aaron C. Treat, Rochester, MN (US); Bruce R. Kline, Winona, MN (US); Michael B. Larson, Red Wing, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 494 days.

This patent is subject to a terminal disclaimer.

(21) Appl. No.: 17/380,525

(22) Filed: Jul. 20, 2021

(65) Prior Publication Data

US 2022/0000628 A1 Jan. 6, 2022

Related U.S. Application Data

(63) Continuation of application No. 16/253,607, filed on Jan. 22, 2019, now Pat. No. 11,096,792, which is a
(Continued)

(51) Int. Cl.
*A61F 2/40* (2006.01)
*A61F 2/46* (2006.01)
*A61F 2/30* (2006.01)

(52) U.S. Cl.
CPC .......... *A61F 2/4014* (2013.01); *A61F 2/4684* (2013.01); *A61F 2002/30378* (2013.01);
(Continued)

(58) Field of Classification Search
CPC .......... A61F 2/4014; A61F 2002/30378; A61F 2002/4037; A61F 2002/4044
See application file for complete search history.

(56) References Cited

U.S. PATENT DOCUMENTS 5,358,526 A 10/1994 Tornier
5,665,090 A 9/1997 Rockwood et al.
(Continued)

FOREIGN PATENT DOCUMENTS

EP 0903128 A1 3/1999
EP 1402856 A1 3/2004
(Continued)

OTHER PUBLICATIONS

Definition of "press fit" retrieved from https://www.merriam-webster.com/dictionary/press fit on Feb. 23, 2024. (Year: 2024).*
(Continued)

*Primary Examiner* — Megan Y Wolf
(74) *Attorney, Agent, or Firm* — Quarles & Brady LLP

(57) ABSTRACT

Methods and devices are disclosed for joint (e.g., shoulder) arthroplasty. In one aspect, there is provided a device for determining inclination and/or version of a prosthetic head with respect to a prosthetic stem. In another aspect, there is provided a joint (e.g., shoulder) prosthesis. In another aspect, there is provided a method for setting an inclination angle and/or a version angle of a prosthetic head with respect to a stem implanted or to be implanted in a bone of a joint (e.g., shoulder).

22 Claims, 8 Drawing Sheets

Related U.S. Application Data continuation of application No. 14/773,605, filed as application No. PCT/US2014/020308 on Mar. 4, 2014, now Pat. No. 10,226,349.

(60) Provisional application No. 61/774,969, filed on Mar. 8, 2013.

(52) U.S. Cl.
CPC ............ *A61F 2002/30538* (2013.01); *A61F 2002/30617* (2013.01); *A61F 2002/4037* (2013.01); *A61F 2/4637* (2013.01)

(56) References Cited

U.S. PATENT DOCUMENTS

| | | | |
|---|---|---|---|
| 6,197,062 | B1 | 3/2001 | Fenlin |
| 6,203,575 | B1 | 3/2001 | Farey |
| 6,228,120 | B1 | 5/2001 | Leonard et al. |
| 6,676,705 | B1 | 1/2004 | Wolf |
| 6,719,799 | B1 | 4/2004 | Kropf |
| 7,097,663 | B1 | 8/2006 | Nicol et al. |
| 7,175,663 | B1 | 2/2007 | Stone |
| 8,002,838 | B2 | 8/2011 | Klotz |
| 8,052,758 | B1 | 11/2011 | Winslow |
| 8,771,362 | B2 | 7/2014 | Isch et al. |
| 9,918,854 | B2 | 3/2018 | Bonin, Jr. |
| 10,226,349 | B2 | 3/2019 | Sperling et al. |
| 10,449,054 | B2 | 10/2019 | Hopkins |
| 11,096,792 | B2 * | 8/2021 | Sperling ............... A61F 2/4684 |
| 2003/0028253 | A1 | 2/2003 | Stone |
| 2004/0064188 | A1 | 1/2004 | Ball et al. |
| 2004/0030400 | A1 | 2/2004 | Horber |
| 2004/0210317 | A1 | 10/2004 | Maroney et al. |
| 2007/0050040 | A1 | 3/2007 | Guederian et al. |
| 2007/0162140 | A1 * | 7/2007 | McDevitt ............... A61F 2/4014 623/908 |
| 2011/0060418 | A1 | 3/2011 | Bailey et al. |
| 2012/0078375 | A1 | 3/2012 | Smith |
| 2014/0222153 | A1 * | 8/2014 | Bonin, Jr. ............. A61F 2/4657 606/86 R |
| 2014/0288657 | A1 | 9/2014 | Lederman et al. |
| 2015/0150687 | A1 | 6/2015 | Hopkins |
| 2016/0030187 | A1 | 2/2016 | Sperling et al. |
| 2020/0000600 | A1 | 1/2020 | Hopkins |

FOREIGN PATENT DOCUMENTS

| | | |
|---|---|---|
| WO | WO 2009/106867 A1 | 9/2009 |
| WO | WO 2012/125795 | 9/2012 |

OTHER PUBLICATIONS

Biomet Orthopedics, Comprehensive Total Shoulder System, Featuring Comprehensive Access Glenoid Instrumentation, Surgical Technique, Copyright 2012 Biomet Orthopedics, 56 pages.

International Search Report and Written Opinion as mailed on Jun. 10, 2014 for International Application No. PCT/US2014/020308.

DePuy, Global Advantage, Shoulder Arthroplasty System, Surgical Technique, Product Brochure, Copyright DePuy Interntional Ltd. and DePuy Orthopaedics, Inc. 2013, 32 pages.

DePuy Synthes, Global AP, Adjustable Prosthesis, Surgical Technique, Product Brochure, Copyright DePuy International Ltd. and DePuy Orthopaedics, Inc. 2013, 52 pages.

European Patent Office, Partial Supplementary European Search Report, Application No. 14760202.3, Feb. 8, 2017.

Extended European Search Report for patent application No. EP 14760202.3, Jul. 24, 2017; 11 pages.

Tonier, Inc., Aequalis Ascend Shoulder System, Product Brochure, Copyright 2013 Tonier, Inc., 3 pages.

Zimmer, Inc., Anatomical Shoulder System, Surgical Technique, Product Brochure, Rev. 6, Copyright 2009, 2010, 2011 Zimmer, Inc., 32 pages.

* cited by examiner

SHOULDER PROSTHESIS WITH VARIABLE INCLINATION HUMERAL HEAD COMPONENT

CROSS-REFERENCES TO RELATED APPLICATIONS

This application is a continuation of U.S. patent application Ser. No. 16/253,607, filed Jan. 22, 2019, which is a continuation of U.S. patent application Ser. No. 14/773,605, filed Sep. 8, 2015, now U.S. Pat. No. 10,226,349 and titled SHOULDER PROSTHESIS WITH VARIABLE INCLINATION HUMERAL HEAD COMPONENT, which is the § 371 U.S. National Stage Application of International Application No. PCT/US2014/020308, titled SHOULDER PROSTHESIS WITH VARIABLE INCLINATION HUMERAL HEAD COMPONENT, filed Mar. 4, 2014, which claims the benefit under 35 U.S.C. § 119(e) of U.S. Provisional Patent Application No. 61/774,969, filed on Mar. 8, 2013 and titled SHOULDER PROSTHESIS WITH VARIABLE INCLINATION HUMERAL HEAD COMPONENT, which are hereby incorporated by reference in their entireties.

STATEMENT REGARDING FEDERALLY SPONSORED RESEARCH

Not Applicable.

BACKGROUND OF THE INVENTION

1. Field of the Invention

The invention relates to a prosthesis and method for variable inclination and/or version of the humeral head component for shoulder arthroplasty, glenosphere for the shoulder, radial head for the elbow, or femoral head for hip arthroplasty.

2. Description of the Related Art

Various prostheses for the replacement of the shoulder joint are known. In one example shoulder prosthesis, the upper portion of the humerus is replaced by a humeral component including (i) a stem, or cleat, that extends into a bore formed within the humerus and (ii) a generally hemispherical head portion that is connected to the stem. The hemispherical head of the humeral component articulates with a complementary concave section of a glenoid component mounted within the glenoid cavity of the scapula. This type of shoulder prosthesis may be called a "primary" or "total" prosthesis. In another example shoulder prosthesis, often called a hemiarthroplasty, a hemispherical head of the humeral component articulates with the native glenoid. In another example shoulder prosthesis, often called a "reverse" or "inverted" prosthesis, the glenoid component includes a convex section that articulates with a complementary concave section of the head of the humeral component.

There has been demonstrated to be a significant theoretical as well as practical need to have variable inclination of the humeral component in shoulder arthroplasty. This has been demonstrated in strong marketplace acceptance as well as a clear demand for this feature in shoulder arthroplasty. Elbow and hip arthroplasty shares a similar need for variable adjustments. In addition, there is a future trend toward patient specific instrumentation in shoulder, elbow, and hip arthroplasty. Variable inclination would be a very desirable, if not necessary, component of any shoulder arthroplasty system to allow the surgeon to exactly match the inclination chosen for the humeral head component on the pre-operative plan and to match the instrumentation for that individual patient.

However, a review of competitive systems in the marketplace reveals that the range of inclination provided by these systems does not properly address the range of humeral head component inclination encountered at the time of shoulder arthroplasty. In addition, many of the ranges provided by shoulder arthroplasty systems are not physiologic and may result in significant component malposition. The range of inclination in currently available systems appears randomly chosen without a true anatomic basis.

In addition to a lack of understanding of the proper range of inclination necessary for a humeral component, the method to achieve this inclination has associated challenges. There are several potential strategies to change the inclination of the humerus available in the marketplace. Each of these methods has disadvantages.

One can manufacture a variety of humeral stems that have a fixed amount of inclination. However, this can result in a significant increase in inventory requiring multiple stem inclinations for a wide breadth of stem diameters.

In one alternative method, a set screw can be used within the stem to lock in the inclination angle of the humeral component. This can make the set screw the "weak link" in the design and could be problematic during attempted removal.

In another alternative method, one can use a screw through a lateral opening in the humeral stem and into the humeral head component to fix the amount of inclination. This can result in making humeral head component removal impossible without removing the humeral stem. This system may be used without the set screw; however, the manufacturer recommends impacting the head and stem together prior to insertion in the humerus. However, the lateral opening in the humeral stem remains, making removal of the humeral stem much more difficult if used with cement.

In yet another alternative method, complex assembly can be performed with a locking mechanism connecting the humeral stem and humeral head component requiring more than ten steps. This method also does not allow one to place the stem in the humeral canal independent of the humeral head component. This decreases the ability to place sutures in the rotator interval and may have an effect on stability and outcome.

Thus, there exists a need for an improved prosthesis and method that provide for variable inclination and/or version of the humeral head component in shoulder arthroplasty, as well as a need for variability in elbow and hip arthroplasty.

SUMMARY OF THE INVENTION

The present invention addresses the foregoing needs by providing improved methods and devices for joint (e.g., shoulder) arthroplasty. There is provided a joint (e.g., shoulder) prosthesis. There is also provided a device for determining inclination and/or version of a prosthetic head with respect to a prosthetic stem. There is also provided a method for setting an inclination angle and/or a version angle of a prosthetic head with respect to a stem implanted or to be implanted in a bone of a joint (e.g., shoulder).

In one aspect, the invention provides a joint prosthesis including a stem dimensioned to be implanted in a first bone of a joint of a subject; a prosthetic head having an outer surface dimensioned for articulation with an articular surface of a natural or artificial joint surface of a second bone of the joint; an adapter dimensioned to be impacted into a depression in an end surface of the prosthetic head opposite the outer surface of the prosthetic head thereby forming an interference fit between the adapter and the depression; and a mounting stud having a first end and a second end wherein the first end is dimensioned for impaction into a socket in the adapter thereby forming an interference fit between the first end and the socket, and the second end is dimensioned for insertion into an opening in the stem.

In one version of the joint prosthesis, the second end of the mounting stud is dimensioned for impaction into the opening in the stem thereby forming an interference fit between the second end and the stem.

In another version of the joint prosthesis, the first end of the mounting stud includes a spherical surface. The spherical surface of the first end of the mounting stud can be rotated in the socket to set inclination and/or version of the head with respect to the stem before forming the interference fit between the first end of the mounting stud and the socket.

In another version of the joint prosthesis, the second end of the mounting stud includes an outer surface that tapers inward from an intermediate section to an outermost section of the second end of the mounting stud.

In another version of the joint prosthesis, the mounting stud includes circumferential reference indicia at or adjacent a junction of the spherical surface of the first end of the mounting stud and the outer surface of the second end of the mounting stud.

In another version of the joint prosthesis, a longitudinal axis of the second end of the mounting stud forms an oblique angle with respect to an axis of the prosthetic head when the interference fit is formed between the first end and the socket.

In another version of the joint prosthesis, the socket of the adapter is offset with respect to a central longitudinal axis of the adapter.

In another version of the joint prosthesis, the adapter has a circular outer surface and the depression has a circular inner surface such that the adapter can be rotated in the depression to set radial offset of the head with respect to the stem before forming the interference fit between the adapter and the depression.

In another version of the joint prosthesis, the head includes at least one first reference marking for alignment with a second reference mark on the adapter.

The joint prosthesis is suitable for use in different joints. For example, the first bone may be the humerus, and the second bone may be the scapula. The first bone may be the scapula, and the second bone may be the humerus. The first bone may be the femur, and the second bone may be the pelvis. The first bone may be the humerus, and the second bone may be the radius.

In another aspect, the invention provides a device for determining an inclination and/or a version of a prosthetic head with respect to a stem wherein the inclination and/or the version are used when the prosthetic head is coupled to the stem. The prosthetic head has an outer surface for articulation with an articular surface of a natural or artificial joint surface of a bone of a joint of a subject. The device can include a body having a well; and a joint element having a first end and a second end wherein the first end is positioned in the well, and the second end is movable between positions wherein a longitudinal axis of the second end is angled with respect to an axis of the body.

One version of the device includes a retainer having an opening extending between a first side and an opposed second side of the retainer wherein the retainer is arranged in the well, and the retainer is dimensioned for translation in the well. The first end of the joint element is dimensioned to be positioned between the body and the first side of the retainer such that the second end of the joint element extends through and outwardly of the opening of the retainer, and the second end of the joint element is dimensioned to be movable between positions where the longitudinal axis of the second end is angled with respect to an axis of the opening of the retainer. The retainer can have an oblong shape with a pair of parallel sides.

Another version of the device includes a fastener movable between a first position in which the fastener allows the retainer to translate in the well and a second position in which the fastener prevents translation of the retainer in the well. The fastener may be a screw that when in the second position causes the first end of the joint element to be immobilized between the body and the retainer.

In one version of the device, the first end of the joint element includes a spherical bearing surface, and the second end of the joint element includes an outer diameter that decreases from an intermediate section to an outermost section of the second end of the joint element. The second end of the joint element may be dimensioned to contact an inner surface of an opening in the stem.

In one version of the device, the body and the retainer include reference markings for determining a positional relationship of the retainer with respect to the body.

The device is suitable for determining an inclination and/or a version of a prosthetic head with respect to a stem of a prosthesis for different joints. For example, the prosthetic head may articulate with the scapula when the joint is the shoulder. The prosthetic head may articulate with the humerus when the joint is the shoulder. The prosthetic head may articulate with the pelvis when the joint is the hip. The prosthetic head may articulate with the radius when the joint is the elbow.

In another aspect, the invention provides a method for setting an inclination angle and/or a version angle of a prosthetic head with respect to a stem implanted or to be implanted in a bone of a joint of a subject. The method uses a trial device including (i) a body having a well, and (ii) a joint element having a first end and a second end wherein the first end is positioned in the well, and the second end is movable between positions wherein a longitudinal axis of the second end is angled with respect to an axis of the body. The second end of the joint element is inserted in an opening in the stem, and the joint element is immobilized with respect to the body. A mounting stud is secured to the prosthetic head in a fixed position with respect to the prosthetic head so as to match an orientation of the immobilized joint element with respect to the body. An end of the mounting stud may be secured in the opening in the stem.

In one version of the method, the trial device further includes a retainer arranged in the well, and the first end of the joint element may be immobilized between the body and the retainer. The retainer may be dimensioned for translation in the well, and the method may comprise preventing translation of the retainer in the well. A fastener may be movable into a position in which the fastener prevents translation of the retainer in the well.

In another version of the method, a template is placed over the immobilized joint element, and a position of a reference line on the template with respect to a first reference point on the body is noted. The template is then placed over the mounting stud, and the reference line is aligned with a second reference point on the prosthetic head. The mounting stud is then secured to the prosthetic head in the fixed position with respect to the prosthetic head. The template may include an opening, and the opening may be placed over the immobilized joint element before noting the position of the reference line on the template with respect to the first reference point on the body. The opening may be placed over the mounting stud before aligning the reference line with the second reference point on the prosthetic head.

In another version of the method, the mounting stud can be moved to a first angle with respect of the prosthetic head before the mounting stud is secured to the prosthetic head in the fixed position. The first angle is about the same (e.g., ±20°, or ±10°, or ±5°) as a second angle of the immobilized joint element with respect to the body. The first angle can be determined using a first reference circle surrounding the mounting stud, and the second angle can be determined using a second reference circle surrounding the joint element. The first angle can be determined using a first reference circle surrounding the mounting stud and a reference line on the template, and the second angle can be determined using a second reference circle surrounding the joint element and the reference line on the template.

The method is suitable for setting an inclination angle and/or a version angle of a prosthetic head with respect to a stem implanted or to be implanted in a bone of various joints of a subject. The bone can be the scapula, and the joint can be the shoulder. The bone can be the humerus, and the joint can be the shoulder. The bone can be the femur, and the joint can be the hip. The bone can be the humerus, and the joint can be the elbow.

In one non-limiting embodiment, it is an advantage of the invention to use a humeral head assembly with a taper to set the inclination/version of a shoulder prosthesis. This construct allows for the use of a pre-existing stem design. The variable inclination is a part of the humeral head assembly. The use of a taper within the humeral head assembly provides the ability to not only change humeral inclination but also humeral version. This eliminates the need to create a separate humeral stem to allow adjustment for inclination and version. A taper of the humeral head assembly has the ability to rotate and then lock in place at the desired inclination/version in the humeral head. This allows the surgeon to maximize intraoperative flexibility by using one stem design to achieve the desired amount of inclination and version. This has the benefit of decreasing humeral component inventory and allows changing humeral inclination/version without removing the stem.

The proper range of inclination can be established with patient studies in order to properly define the range of inclination that will accommodate patients. This can facilitate the accurate and efficient design of a variable inclination system to determine the exact range of inclination that is necessary for the system.

Adjustment of humeral inclination has become a clear need in the shoulder arthroplasty marketplace. Significant deficiencies have become recognized in the currently available systems including a range of inclinations that are not based on the anatomic distribution. Moreover, the currently available systems used to create variable inclination have significant technical drawbacks. Therefore, the method of the invention has been designed to address these significant market needs. In addition, applications that may benefit from similar adjustability include the glenosphere of the shoulder, radial head of the elbow, femoral head of the hip, and the like.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
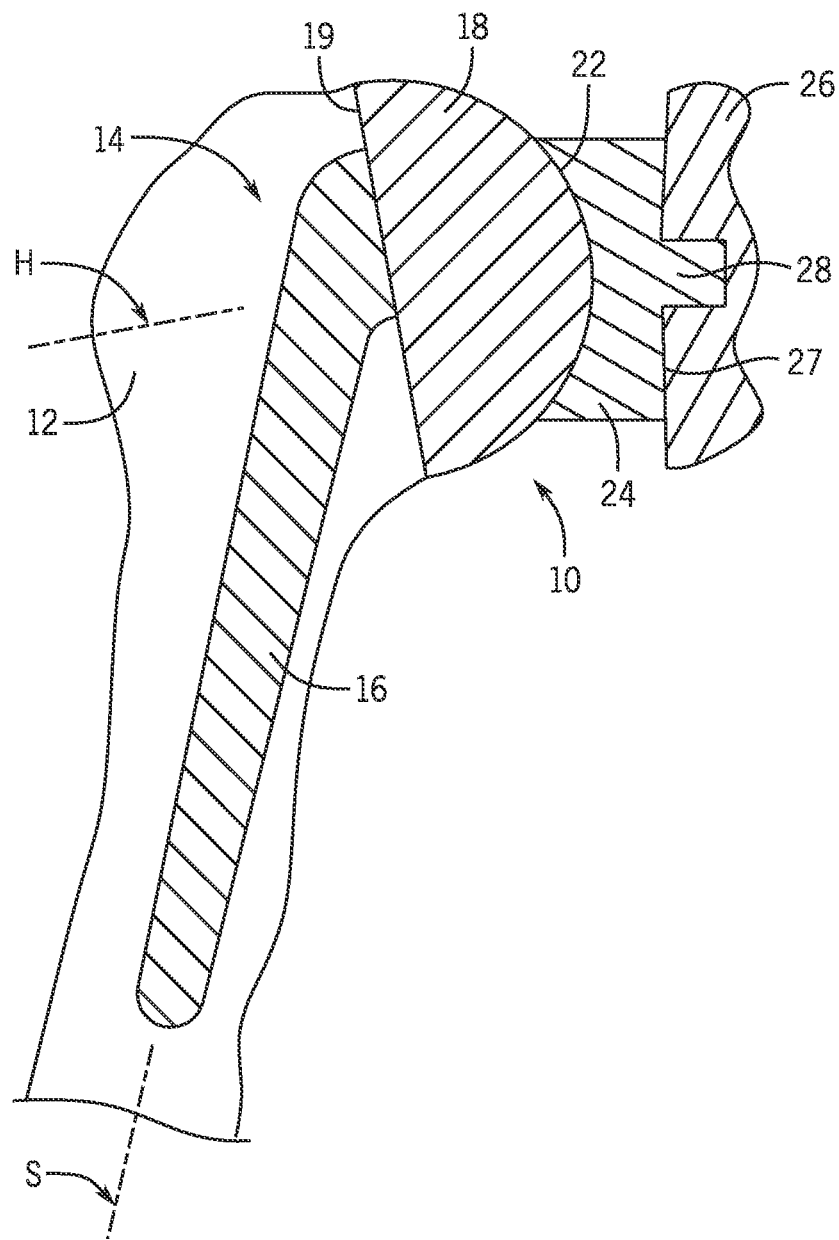
FIG. 1 is a cross-sectional view of a conventional shoulder prosthesis.

Looking first at FIG. 1, there is shown an example conventional shoulder prosthesis 10. The upper portion of the humerus 12 is replaced by a humeral component 14 including a stem 16 that extends into a bore formed within the humerus 12. Typically, the stem 16 is fixed within the bore formed within the humerus 12. The stem 16 has a longitudinal stem axis S. A generally hemispherical head 18 is connected to the stem 16. Alternatively, the head 18 is integral with the stem 16. The hemispherical head 18 has a base surface 19 and a longitudinal head axis H. The hemispherical head 18 of the humeral component 14 articulates with a complementary concave section 22 of a glenoid component 24 that is fixed within the glenoid cavity of the scapula 26 using cemented or uncemented posts 28. The glenoid component 24 includes a base surface 27 opposite the concave section 22 that serves as an articular surface of the glenoid component 24.

Figures 2, 3:
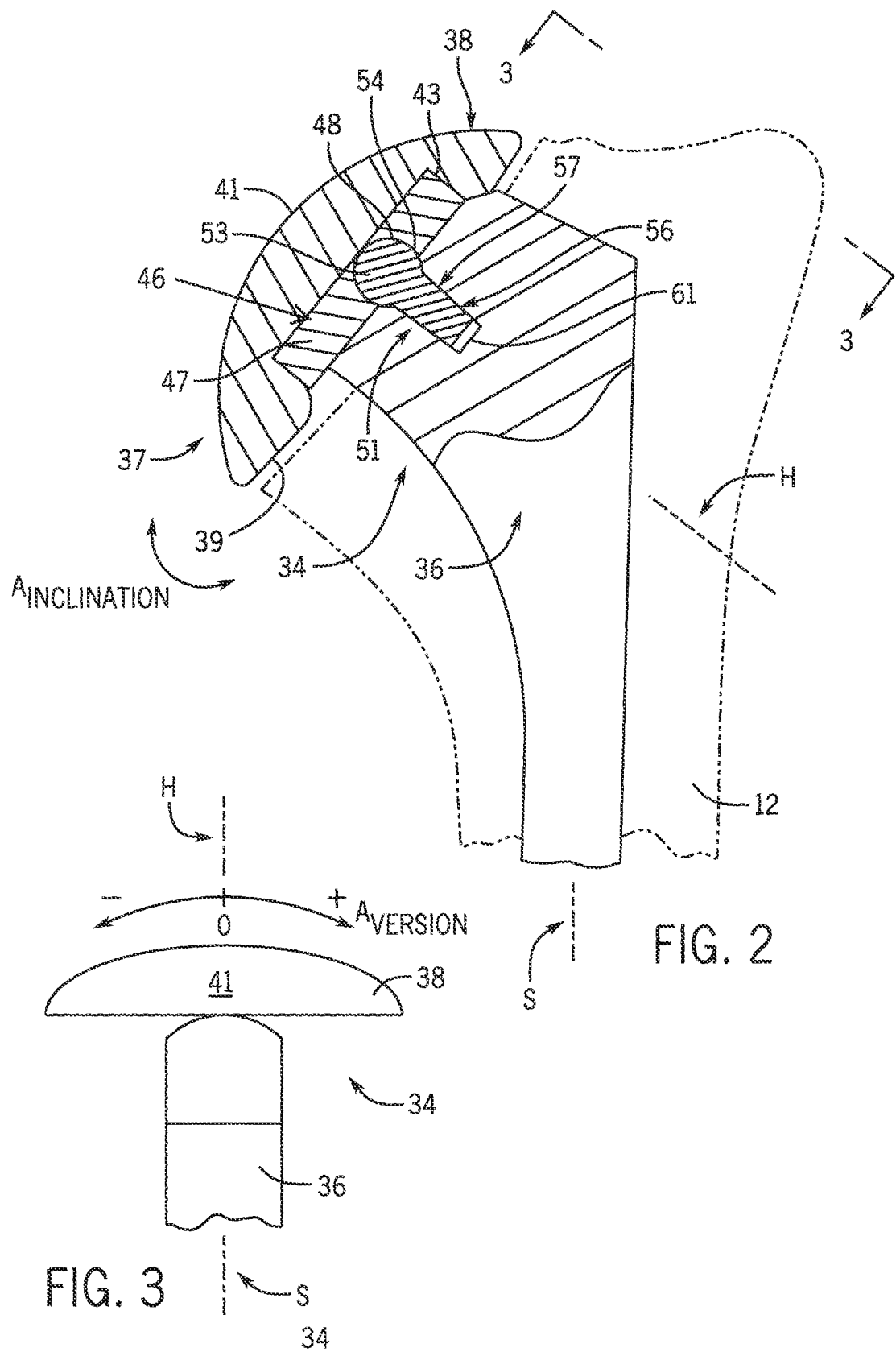
FIG. 2 is an anterior view, partially in cross section, of one embodiment of a shoulder prosthesis according to the invention.
FIG. 3 is a view of the shoulder prosthesis of FIG. 2, taken along line 3-3 of FIG. 2.

Referring now to FIGS. 2-3, there is shown an example embodiment of a shoulder prosthesis according to the invention. The humeral component 34 includes a stem 36 that extends into a bore formed within the humerus 12. The stem 36 has a longitudinal stem axis S. A humeral head assembly 37 has a generally hemispherical head 38. The humeral head assembly 37 is connected to the stem 36. The outer surface 41 of the hemispherical head 38 of the humeral component 34 articulates with a complementary concave section 22 of a glenoid component 24 that is fixed within the glenoid cavity of the scapula 26 as shown in FIG. 1. In the humeral head assembly 37, the head 38 includes a depression 43 that receives an adapter 46 having a body 47 with a socket 48 that is eccentric, i.e., the central axis of the socket 48 is offset from the central axis of the body 47. The humeral head assembly 37 also includes a mounting stud 51 having a first end 53 with a spherical bearing surface 54 and a second end 56 comprising a tapered shaft 57. The first end 53 of the mounting stud 51 is secured in the socket 48 of the adapter body 47 by way of an interference fit formed by impacting the mounting stud 51 in the socket 48. The second end 56 of the mounting stud 51 is secured in a stem opening 61 of the stem 36 by way of a taper lock formed by impacting the mounting stud 51 in the stem opening 61.

The parts of the humeral component 34 may be formed from, for example: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). The prosthetic component can be manufactured by machining an article formed from these materials, or by molding these materials in a suitable mold.

In FIG. 2, taking the included angle in an anterior view between stem axis S and head axis H in degrees and subtracting from 180° is one way to define the inclination angle $A_{inclination}$ of the humeral head 38 in degrees. The inclination angle of the humeral head 38 can be adjusted to have a selected angle between the longitudinal head axis H and the longitudinal stem axis S by assembling the humeral head assembly 37 with the socket 48 of the adapter body 47 in a selected position with respect to the head 38 and with the mounting stud 51 in a selected orientation in the socket 48 of the adapter body 47 as described below.

In FIG. 3, taking the included angle in a medial view between stem axis S and head axis H in degrees is one way to define the version angle $A_{version}$ of the humeral head 38 in degrees. The version angle of the humeral head 38 can be expressed as a positive or negative angle with respect to the stem axis S. The version angle of the humeral head 38 can be adjusted to have a selected positive or negative angle between the longitudinal head axis H and the longitudinal stem axis S by assembling the humeral head assembly 37 with the socket 48 of the adapter body 47 in a selected position with respect to the head 38 and with the mounting stud 51 in a selected orientation in the socket of the adapter body 47 as described below.

Referring now for FIGS. 4-9, a surgeon can implant the humeral component 34 so that the humeral component 34 articulates with a complementary concave section 22 of a glenoid component 24. The fixing of the glenoid component 24 within the glenoid cavity of the scapula 26 can be done in a conventional manner. A method of the invention uses a trial head assembly 63 (see FIG. 4). A trial head assembly 63 is prepared, and then the orientation of the adapter 46 and the mounting stud 51 of the humeral head assembly 37 are matched to the trial head assembly 63.

The trial head assembly 63 includes a body 65. Looking at FIG. 4, one side of the body 65 has an generally oblong shaped well 66 with offset markings 67 (A, B, C, D, E) on parallel side sections of the well 66. Opposite the side of the body 65 having the well 66, there is a side of the body 65 that has a generally hemispherical surface identical or substantially similar to the outer surface 41 of the hemispherical head 38 of the humeral component 34. A retainer 69 can slide in the well 66 of the body 65 as shown at L in FIG. 4. In the trial head assembly 63, set screws 70 can lock the position of the retainer 69 in the well 66. The oblong shape of the well 66 may prevent the retainer 69 from rotating within the well 66 while set screws 70 are tightened (similarly, pins, and the like, may be used that slide along tightly-clearanced slots to prevent rotation of the retainer 69). The retainer 69 has an opening 71, and cross hair markings 72. A ball joint element 75 of the trial head assembly 63 has a first end 77 with spherical bearing surface 78 and a second end 79 in the shape of a tapered shaft 80. The second end 79 of the ball joint element 75 protrudes outwardly through the retainer opening 71, and the first end 77 of the ball joint element 75 is positioned between the retainer 69 and the surface of the well 66. When the set screws 70 are tightened, the second end 79 of the ball joint element 75 is secured by contact with a surface of the retainer 69 and the surface of the well 66. Three concentric reference circles 81 surround the ball joint element 75 near the junction of the spherical bearing surface 78 and the tapered shaft 80.

Figure 5:
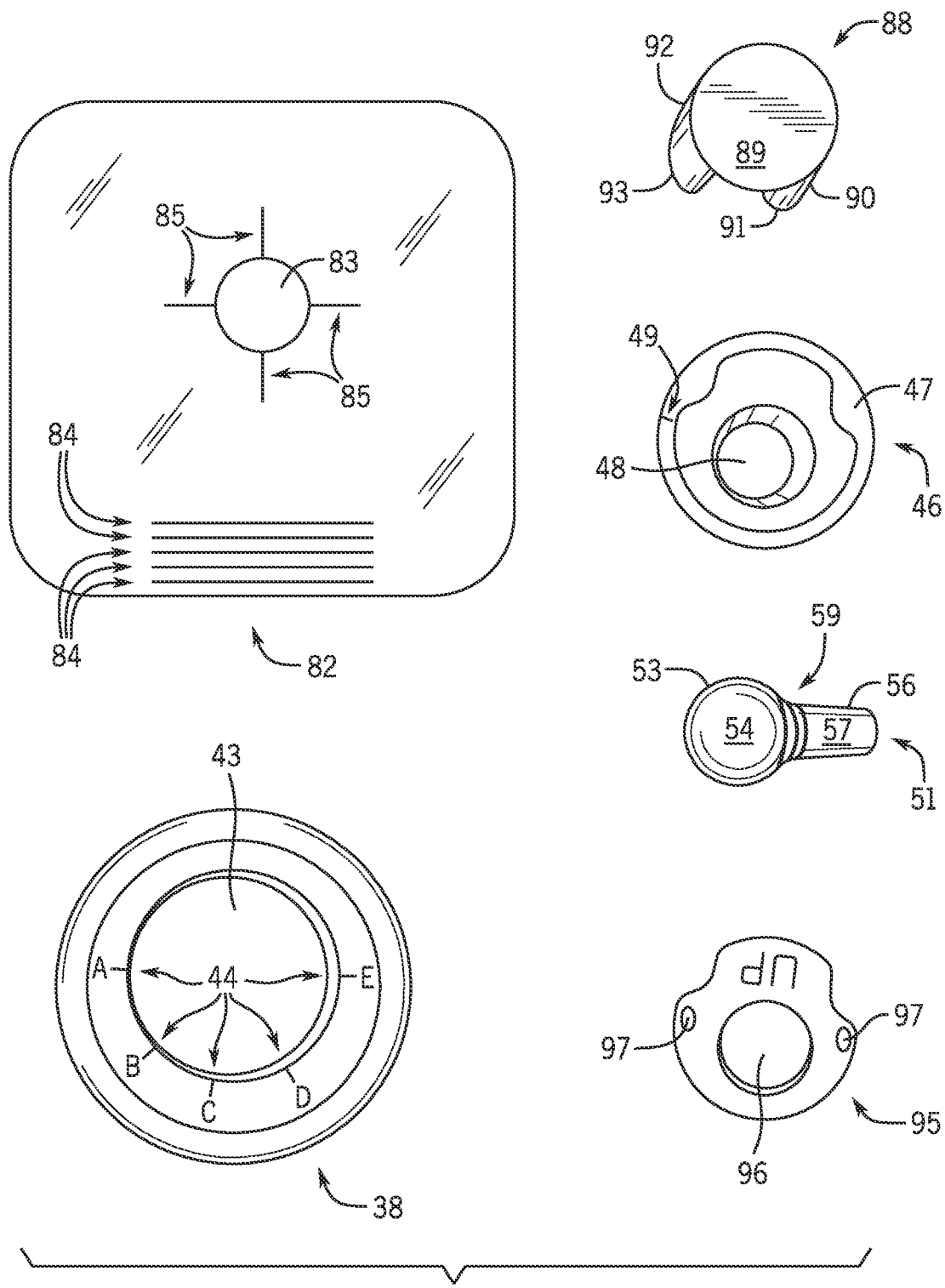
FIG. 5 shows a template and components of a humeral head assembly kit of a shoulder prosthesis according to the invention.

Shown in FIG. 5 is a transparent template 82 that can be used to match the orientation of the components of the humeral head assembly 37 and the trial head assembly 63. The template 82 has an opening 83, reference lines 84, and cross hair markings 85. The template 82 may take other forms, such as a platform with a non-marring, low-friction surface for the head to rest upon while it is being rotated to its maximum offset, while still retaining an opening 83, and reference lines 84.

Preparing the trial head assembly 63 begins with ensuring that the two set screws 70 on the trial head assembly 63 are loose. One verifies that the ball joint element 75 rotates freely in all directions and the retainer 69 slides freely in the well 66. The stem 36 is fixed within a bore formed within the humerus 12 (see FIG. 2). The second end 79 of the ball joint element 75 is then seated in the stem opening 61 of the stem 36 which has been implanted in the humerus 12 of a patient. The body 65 of the trial head assembly 63 is adjusted to the desired radial offset, inclination and/or version in the patient, and the two set screws 70 are tightened to lock the offset and the angle of the ball joint element 75 of the trial head assembly 63. The set screws 70 are accessible on a side of the body 65 opposite the retainer 69. The trial head assembly 63 is then removed from the stem 36.

Figure 4:
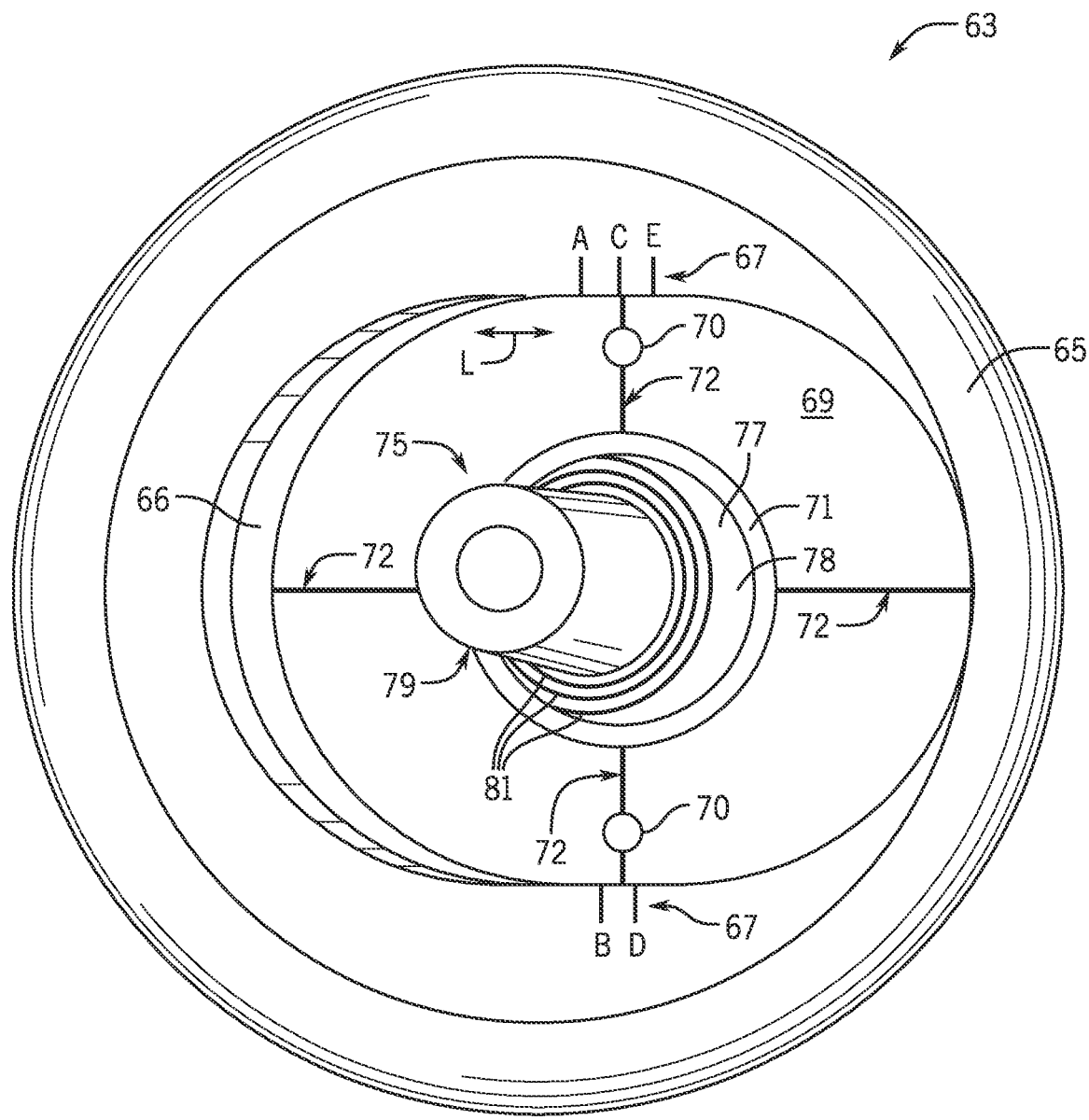
FIG. 4 is a bottom view of a trial head assembly used in implanting a shoulder prosthesis according to the invention.

The trial head assembly 63 is then turned upside-down such that the retainer 69 and the ball joint element 75 are visible to the surgeon as in FIG. 4. The surgeon notes the four cross-hair markings 72 on the surface of the retainer 69, ninety degrees apart. The offset is indicated by the position of the vertical markings of the cross hair markings 72 of the retainer 69 relative to the A, B, C, D, and E offset markings 67 on the body 65. The surgeon also notes a reference angle indicated by the concentric reference circles 81 on the ball joint element 75. In the non-limiting example configuration shown, there are three concentric reference circles 81 present on the ball joint element 75, which can be of different colors such as black, red, and blue. The reference angle is read by noting the position of the concentric reference circles 81 at the location where one of the cross-hair markings 72 would intersect the inner opening 71 circumference of the retainer 69. By noting the position of the concentric reference circles 81 at two of these orthogonal locations (i.e., two adjacent cross-hair markings 72), the reference angle is fully characterized.

The humeral head assembly 37 is assembled to match the orientation of the ball joint element 75 in the trial head assembly 63. The adapter 46 is inserted into the head 38, and the adapter 46 is rotated so that the offset reference markings 44 on the head 38 align with the appropriate offset reference mark 49 on the adapter 46. See FIG. 6.

Figure 6:
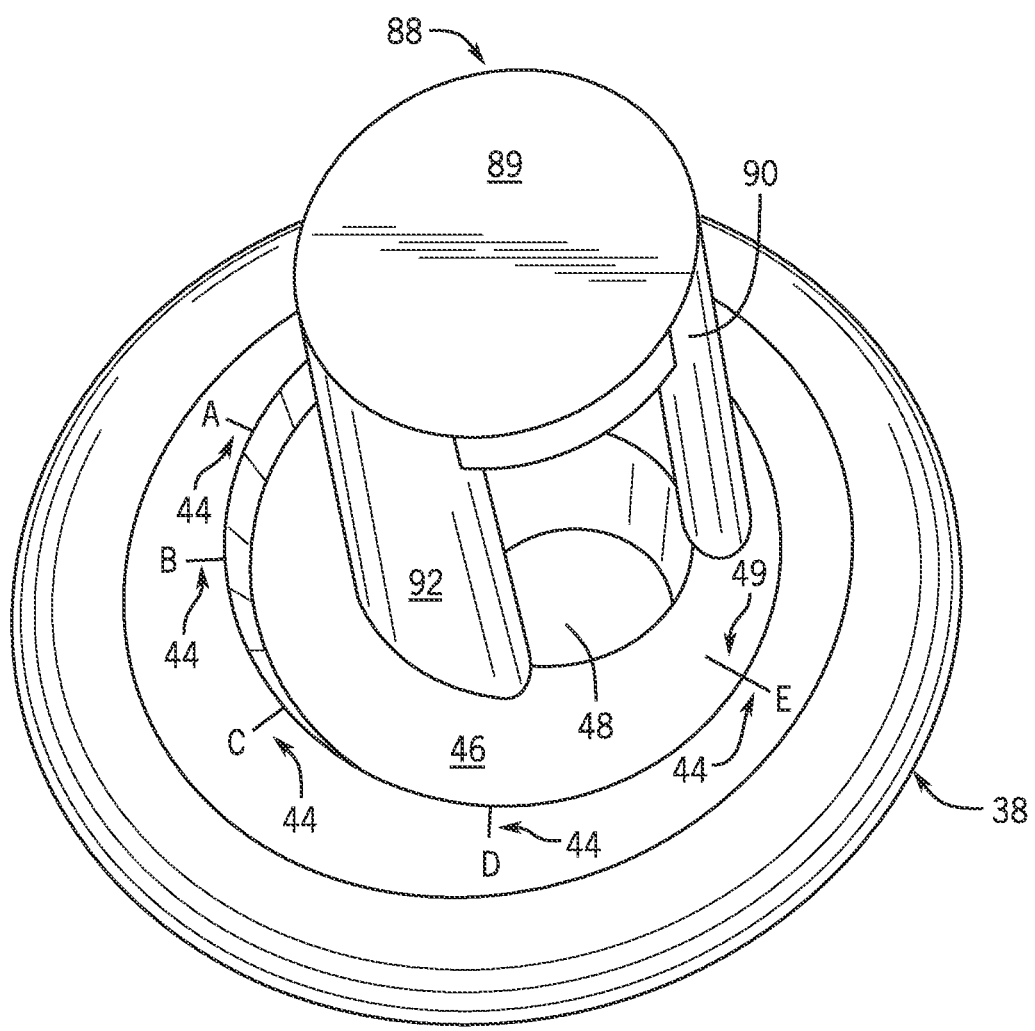
FIG. 6 is a top perspective view of a step in assembling a humeral head assembly of a shoulder prosthesis according to the invention.

Still referring to FIG. 6, an impactor 88 is then used in the method of the invention. The impactor 88 has a round flat end surface 89, a first side wall 90 with an end surface 91, and a second side wall 92 with an end surface 93. The end surfaces 91, 93 of the impactor 88 are placed on top of adapter 46, and a mallet is used to strike the flat end surface 89 of the impactor 88 to seat the adapter 46 inside the depression 43 of the head 38.

Figure 7:
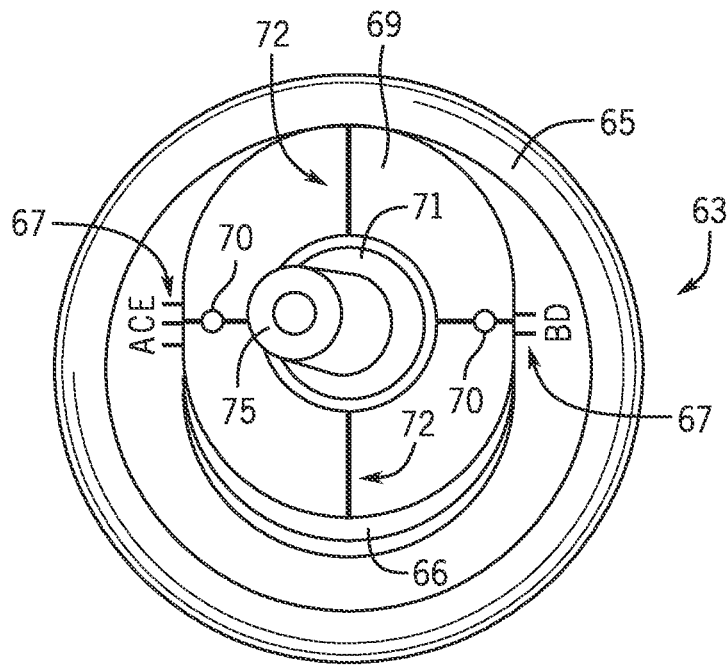
FIG. 7 is a top view of a step, subsequent to FIG. 6, in assembling a humeral head assembly of a shoulder prosthesis according to the invention.
Figure 7:
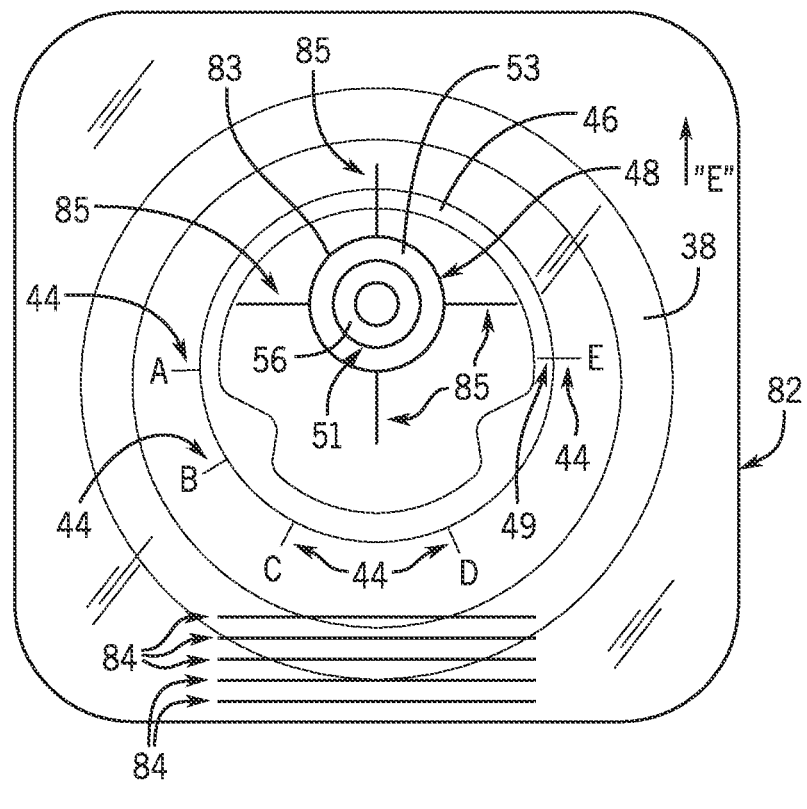

Looking at FIG. 7, the first end 53 of the mounting stud 51 is placed vertically onto the socket 48 of the adapter 46, and the mounting stud 51 is pressed down using just enough force to barely seat it. The socket 48 may also be lined with a material, such as rubber, that may act to hold the stud 51 in place. The opening 83 of the transparent template 82 is placed over the second end 56 of the mounting stud 51, and the reference lines 84 of the template 82 are used to align the maximum offset direction of the head 38 with the maximum offset direction of the body 65 of the trial head assembly 63. The template 82 is removed, noting its position relative to the head 38. FIG. 7 shows how the trial head assembly 63 can be located adjacent the humeral head assembly 37 during assembly for reference.

Figure 8:
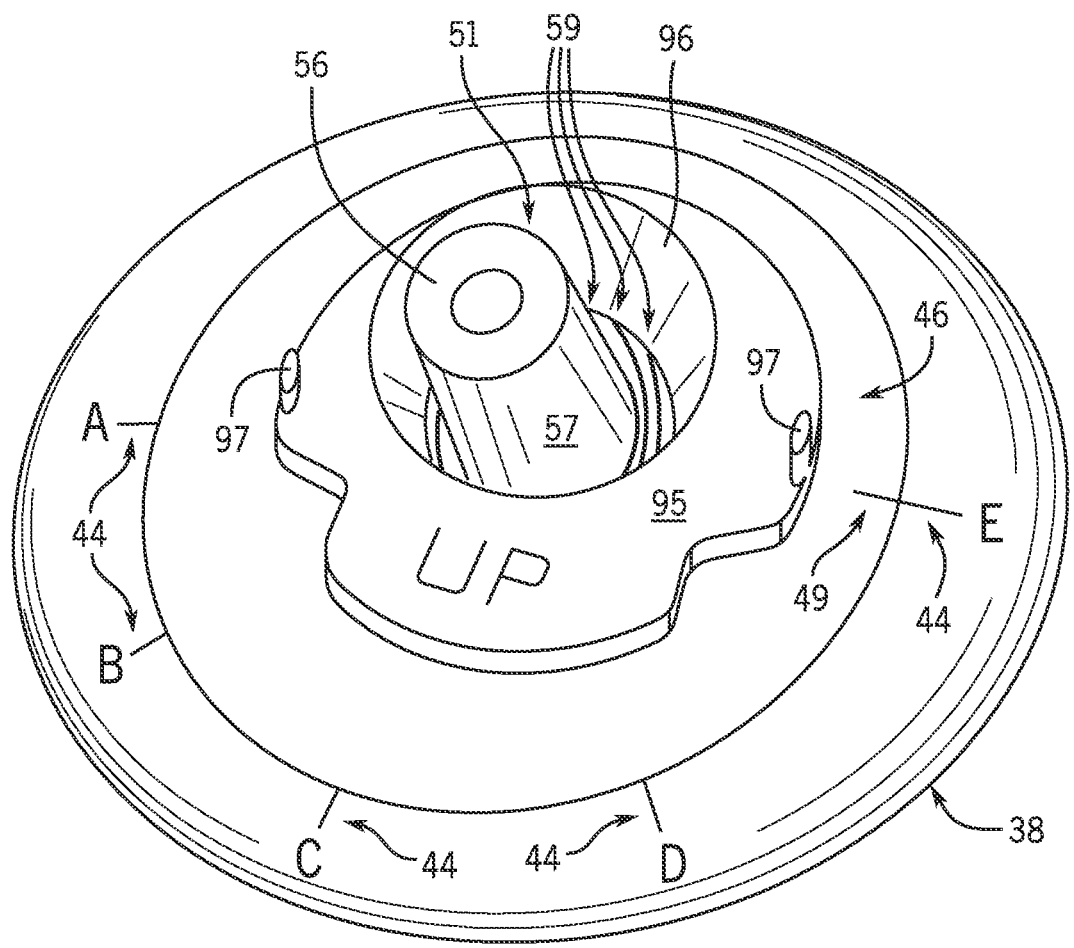
FIG. 8 is a top perspective view of a step, subsequent to FIG. 7, in assembling a humeral head assembly of a shoulder prosthesis according to the invention.

Turning to FIG. 8, an impactor ring 95 having an aperture 96 is placed over the mounting stud 51, and rotated so the impactor ring 95 aligns with the indexing features of the adapter 46. As noted above, the stud 51 should not change orientation during assembly, and the impactor ring 95 may be lined with a material, such as rubber, to prevent motion. The impactor ring 95 is pushed into the pocket of the adapter 46. The template is re-placed over the mounting stud 51 in the same position as when the template 82 was removed. The cross-hair markings 85 on the transparent template 82 are referenced, and the mounting stud 51 is moved to the same angle of the ball joint element 75 of the trial head assembly 63 using concentric reference circles 59 which surround the mounting stud 51 near the junction of the spherical bearing surface 54 and the tapered shaft 57 of the mounting stud 51. The template 82 is then removed.

Figure 9:
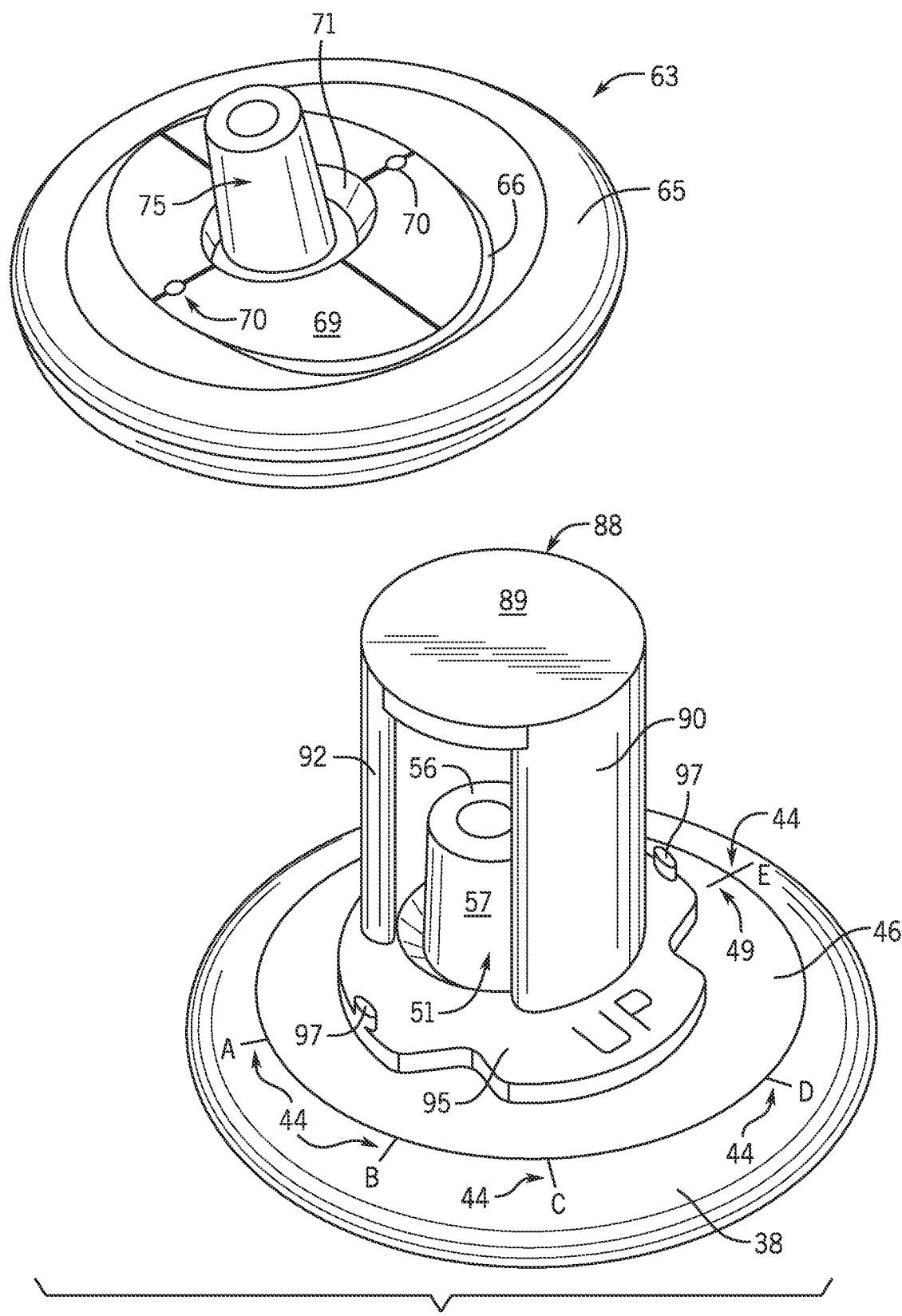
FIG. 9 is a top perspective view of a step, subsequent to FIG. 8, in assembling a humeral head assembly of a shoulder prosthesis according to the invention.

Looking at FIG. 9, the angle of the mounting stud 51 of the head 38 and the ball joint element 75 of the trial head assembly 63 are visually compared by looking at them horizontally from two orthogonal directions. If the angles match acceptably, one gently pushes down on the impactor ring 95, applying even pressure around the mounting stud 51. The impactor ring 95 holds the mounting stud 51 at the correct angle during the subsequent steps. One then visually re-confirms that the angle of the mounting stud 51 of the humeral head assembly 37 is still acceptable.

The impactor 88 is positioned concentric with the impactor ring 95 with the end surfaces 91, 93 of the impactor 88 contacting the impactor ring 95. One uses downward pressure to hold the impactor 88 in place with one hand, and then one strikes the end surface 89 of the impactor 88 with a mallet. This pushes down the impactor ring 95, which in turn drives the mounting stud 51 into an interference fit with the socket 48 of the adapter 46. The interference fit may be enhanced by modifying the surfaces of either the mounting stud 51, or the socket 48, by abrasive blasting, roughening the surfaces, cutting rough machining lines, or adding sharp blade-like structures to engage the opposing surface, and the like, or otherwise modifying the shape of either the mounting stud 51 or the socket 48. The mounting stud 51 is fully seated when the top surface of the impactor ring 95 is approximately flush with the top surface of the adapter 46. One then visually re-confirms that the angle of the mounting stud 51 of the humeral head assembly 37 is still acceptable.

The impactor ring 95 can be removed by pinching two tabs 97 with the thumb and index finger and pulling upward. The humeral head assembly 37 is now ready for implantation. The second end 56 of the mounting stud 51 of the humeral head assembly 37 is secured in a stem opening 61 of the stem 36. Seating the humeral head assembly 37 in the humeral stem 36 using a mallet further seats the assembled components together as in FIG. 2.

Thus, the invention provides an improved prosthesis and method that provide for variable inclination and/or version and/or offset of the humeral head component in shoulder arthroplasty. While a human cadaveric validation has been done with respect to the methods and the shoulder arthroplasty components, the method could be used for other joints (e.g., hip, knee, elbow, foot, ankle, etc. . . . ).

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A joint prosthesis comprising:
an implant dimensioned to be implanted in a first bone of a joint of a subject;
a prosthetic head having an outer surface dimensioned for articulation with an articular surface of a natural or artificial joint surface of a second bone of the joint;
an adapter dimensioned to be impacted into a depression in an end surface of the prosthetic head opposite the outer surface of the prosthetic head thereby forming an interference fit between the adapter and the depression; and
a mounting stud having a first end and a second end, the first end being dimensioned for impaction into a socket in the adapter thereby forming an interference fit between the first end and the socket, the first end of the mounting stud including a spherical surface, the spherical surface extending from a longitudinal axis of the first end of the mounting stud toward the second end of the mounting stud, the second end being dimensioned for insertion into an opening in the implant,
wherein the first end of the mounting stud and the socket are configured to allow for adjustment of an orientation of the prosthetic head relative to the mounting stud over a range of inclination angles before forming the interference fit between the first end of the mounting stud and the socket, and wherein a selected inclination angle within the range of inclination angles is fixed by the interference fit between the first end of the mounting stud and the socket after implantation and in the absence of a fastener.

2. The joint prosthesis of claim 1 wherein:
the second end of the mounting stud is dimensioned for impaction into the opening in the implant thereby forming an interference fit between the second end of the mounting stud and the implant.

3. The joint prosthesis of claim 1 wherein:
the spherical surface of the first end of the mounting stud can be rotated in the socket to set inclination and/or version of the prosthetic head with respect to the implant before forming the interference fit between the first end of the mounting stud and the socket.

4. The joint prosthesis of claim 1 wherein:
the second end of the mounting stud includes an outer surface that tapers inward from an intermediate section to an outermost section of the second end of the mounting stud.

5. The joint prosthesis of claim 4 wherein:
the mounting stud includes circumferential reference indicia at or adjacent a junction of the spherical surface of the first end of the mounting stud and the outer surface of the second end of the mounting stud.

6. The joint prosthesis of claim 1 wherein:
a longitudinal axis of the second end of the mounting stud forms an oblique angle with respect to an axis of the prosthetic head when the interference fit is formed between the first end of the mounting stud and the socket.

7. The joint prosthesis of claim 1 wherein:
the socket of the adapter is offset with respect to a central longitudinal axis of the adapter.

8. The joint prosthesis of claim 7 wherein:
the adapter has a circular outer surface and the depression has a circular inner surface such that the adapter can be rotated in the depression to set radial offset of the prosthetic head with respect to the implant before forming the interference fit between the adapter and the depression.

9. The joint prosthesis of claim 8 wherein:
the prosthetic head includes at least one first reference marking for alignment with a second reference mark on the adapter.

10. The joint prosthesis of claim 1 wherein:
the first bone is the humerus, and
the second bone is the scapula.

11. The joint prosthesis of claim 1 wherein:
the first bone is the scapula, and
the second bone is the humerus.

12. The joint prosthesis of claim 1 wherein:
the first bone is the femur, and
the second bone is the pelvis.

13. The joint prosthesis of claim 1 wherein:
the first bone is the humerus, and
the second bone is the radius.

14. The joint prosthesis of claim 1, wherein the first end of the mounting stud comprises a modified surface configured to enhance the interference fit between the first end of the mounting stud and the socket.

15. The joint prosthesis of claim 14, wherein the modified surface comprises a roughened surface.

16. The joint prosthesis of claim 14, wherein the modified surface comprises machining lines.

17. The joint prosthesis of claim 14, wherein the modified surface comprises structures configured to engage an opposing surface of the socket.

18. The joint prosthesis of claim 1, wherein the socket comprises a modified surface configured to enhance the interference fit between the first end of the mounting stud and the socket.

19. The joint prosthesis of claim 18, wherein the modified surface comprises a roughened surface.

20. The joint prosthesis of claim 18, wherein the modified surface comprises machining lines.

21. The joint prosthesis of claim 18, wherein the modified surface comprises structures configured to engage an opposing surface of the first end of the mounting stud.

22. A joint prosthesis comprising:
an implant dimensioned to be implanted in a first bone of a joint of a subject;
a prosthetic head having an outer surface dimensioned for articulation with an articular surface of a natural or artificial joint surface of a second bone of the joint;
an adapter dimensioned to be impacted into a depression in an end surface of the prosthetic head opposite the outer surface of the prosthetic head thereby forming an interference fit between the adapter and the depression; and
a mounting stud having a first end and a second end, the first end being dimensioned for impaction into a socket in the adapter thereby forming an interference fit between the first end and the socket, the first end of the mounting stud including a spherical surface, the spherical surface extending from a longitudinal axis of the first end of the mounting stud toward the second end of the mounting stud, the second end being dimensioned for insertion into an opening in the implant,
wherein the first end of the mounting stud comprises a modified surface configured to enhance the interference fit between the first end of the mounting stud and the socket, and
wherein the first end of the mounting stud and the socket are configured to allow for adjustment of an orientation of the prosthetic head relative to the mounting stud over a range of inclination angles before forming the interference fit between the first end of the mounting stud and the socket.

* * * * *